(12) United States Patent
Satou et al.

(10) Patent No.: US 10,081,585 B2
(45) Date of Patent: *Sep. 25, 2018

(54) COMPOUND CONTAINING PHENOLIC HYDROXYL GROUP, PHENOLIC RESIN, CURABLE COMPOSITION, CURED PRODUCT THEREOF, SEMICONDUCTOR SEALING MATERIAL, AND PRINTED CIRCUIT BOARD

(71) Applicant: DIC Corporation, Tokyo (JP)

(72) Inventors: Yutaka Satou, Ichihara (JP); Ayumi Takahashi, Ichihara (JP)

(73) Assignee: DIC Corporation, Tokyo (JP)

(*) Notice: Subject to any disclaimer, the term of this patent is extended or adjusted under 35 U.S.C. 154(b) by 153 days.

This patent is subject to a terminal disclaimer.

(21) Appl. No.: 14/897,864

(22) PCT Filed: Feb. 21, 2014

(86) PCT No.: PCT/JP2014/054137
§ 371 (c)(1),
(2) Date: Dec. 11, 2015

(87) PCT Pub. No.: WO2015/199659
PCT Pub. Date: Dec. 18, 2014

(65) Prior Publication Data
US 2016/0122269 A1 May 5, 2016

(30) Foreign Application Priority Data
Jun. 14, 2013 (JP) ................. 2013-125563

(51) Int. Cl.
*C07C 39/14* (2006.01)
*C07C 37/14* (2006.01)
(Continued)

(52) U.S. Cl.
CPC .............. *C07C 39/14* (2013.01); *C07C 37/14* (2013.01); *C08G 8/02* (2013.01); *C08G 59/621* (2013.01);
(Continued)

(58) Field of Classification Search
CPC ...................................... C07C 39/14
(Continued)

(56) References Cited

U.S. PATENT DOCUMENTS

2013/0131215 A1  5/2013  Satou

FOREIGN PATENT DOCUMENTS

JP  10-025287 A  1/1998
JP  2002-114889 A  4/2002
(Continued)

OTHER PUBLICATIONS

U.S. Appl. No. 14/897,850 claims, 2015.*
(Continued)

*Primary Examiner* — Duc Truong
(74) *Attorney, Agent, or Firm* — Locke Lord LLP; James E. Armstrong, IV; Nicholas J. DiCeglie, Jr.

(57) ABSTRACT

There are provided a compound containing a phenolic hydroxyl group, which exhibits excellent heat resistance and excellent flame retardancy in terms of a cured product thereof, a phenolic resin including the same, a curable composition and a cured product thereof, a semiconductor sealing material, and a printed circuit board. The compound containing a phenolic hydroxyl group has a molecular structure represented by the following General Formula (I):

(Continued)

(2013.01); *H01L 23/293* (2013.01); *H01L 23/295* (2013.01); *H05K 1/0373* (2013.01); *H05K 1/09* (2013.01); *C08L 65/00* (2013.01); *H01L 2924/0002* (2013.01)

(58) Field of Classification Search
USPC ........................................................ 428/457
See application file for complete search history.

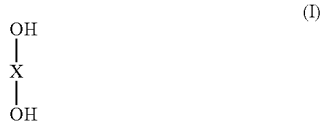

wherein X is a structural site represented by the following Structural Formula (x1) or (x2);

(56) References Cited

FOREIGN PATENT DOCUMENTS

| JP | 2013-023612 A | 2/2013 |
|---|---|---|
| TW | 201219456 A | 5/2012 |

OTHER PUBLICATIONS

Roland Scholl et al., "Die Halochromie des 5-Benzoyl-1,4-naphthohydrochinons," EurJIC, vol. 68, Nov. 6, 1935, pp. 2034-2039 and information sheet. (cited in the corresponding CN OA) (Note: for relevant part see chemical structure VI).

Rudolf Pummerer et al., "Die Kondensation von Chinonen mit Phenolen. (3. Mitteilung uber Diarylchinone)," EurJIC, vol. 60, Jun. 15, 1927, pp. 1442-1451 and information sheet. (cited in the corresponding CN OA) (Note: for relevant part see chemical structure III).

Madhushree Das Sarma et al., "Synthesis and antiproliferative activity of some novel derivatives of diospyrin, a plant-derived naphthoquinonoid," Bioorganic & Medicinal Chemistry, 2007, 15(11), pp. 3672-3677.

Utpal Sanyal et al., "Liquid chromatographic separation of derivatives of diospyrin, a bioactive bisnaphthoquinonoid plant-product, and analogous naphthyl compounds," Journal of Chromatography A, 2003, 1017(1-2), pp. 225-232.

N. Lall et al., "Antimycobacterial activity of diospyrin derivatives and a structural analogue of diospyrin against *Mycobacterium tuberculosis* in vitro," Journal of Antimicrobial Chemotherapy, 2003, 51(2), pp. 435-438.

Melanie T. Cushion et al., "Effects of Atovaquone and Diospyrin-Based Drugs on the Cellular ATP of *Pneumocystis carinii* f. sp. *carinii*," Antimicrobial Agents and Chemotherapy, 2000, 44(3), pp. 713-719.

Hans Brockmann, "Zur cyclo-Trimerisierung von 1,4-Naphthochinon; Kooperieren von Phenol/Chinon-Additionen mit Redoxreaktionen," Liebigs Annalen der Chemie, 1988, 1, pp. 1-7.

Hartmut Laatsch, "Dimere Naphthochinone, XI. Oxidationsprodukte substituierter Binaphthyle," Liebigs Annalen der Chemie, 1984, 7, pp. 1367-1381.

Hans Brockmann, "Regioselektive Synthesen von 3,3'-Bijuglon, Mamegakinon, Dianellinon, cyclo-Trijuglon, Xylospyrin and Trianellinon durch Phenol Chinon-Addition," Liebigs Annalen der Chemie, 1983, 3, pp. 433-447.

Michelle Yu Huay Lai, "Synthetic Studies Towards the Crisamicins," the University of Auckland, Jun. 2002, pp. 83-96 and pp. 214-218.

Rudolf Pummerer et al., "Die Kondensation von Chinonen mit Phenolen," Mitteilung uber Diarylchinone., Berichte der Deutschen Chemischen Gesellschaft [Abteilung] B: Abhandlungen, 1927, 60B, pp. 1442-1451.

Tetsuya Takeya et al., "Reaction of 1-Naphthols with π-Acceptor p-Benzoquinones: Oxidative Aryl Coupling vs. Non-Oxidative Electrophilic Arylation," Chemical & Pharmaceutical Bulletin (2005), 53(2), 199-206.

Attillio Arienti et al., "Highly selective conversion of hydroxylated biaryls to dibenzofuran derivatives over zeolite catalyst," Journal of the Chemical Society, Perkin Transactions 1: Organic and Bio-Organic Chemistry (1997), (9), pp. 1391-1393.

Marko Zupan et al., "Chemistry of Organo Halogenic Molecules. 140. Role of the Reagent Structure of the Transformations of Hydroxy Substituted Organic Molecules with N-Fluoro Class of Fluorinating Reagents," Bulletin of the Chemical Society of Japan (1995), 68(6), pp. 1655-1660.

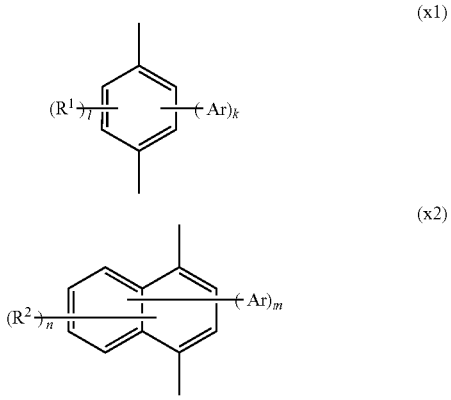

wherein, in Formula (x1) or (x2), k is an integer of 1 to 3, m is 1 or 2, Ar is a structural site represented by the following Structural Formula (Ar1), and in a case where when k or m is 2 or greater, a plurality of Ar's may be the same as or different from each other;

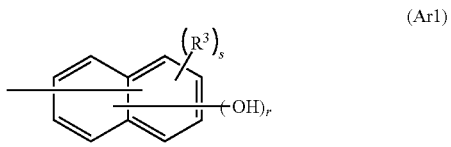

wherein r is 1 or 2.

6 Claims, 3 Drawing Sheets

(51) Int. Cl.

| H01L 23/29 | (2006.01) |
|---|---|
| C08G 61/02 | (2006.01) |
| C08G 8/02 | (2006.01) |
| C08L 61/16 | (2006.01) |
| C08K 3/04 | (2006.01) |
| C08K 7/18 | (2006.01) |
| H05K 1/03 | (2006.01) |
| H05K 1/09 | (2006.01) |
| C08G 59/62 | (2006.01) |
| C08L 63/00 | (2006.01) |
| C08L 91/06 | (2006.01) |
| C07C 37/00 | (2006.01) |
| C08L 65/00 | (2006.01) |

(52) U.S. Cl.
CPC ................ *C08G 61/02* (2013.01); *C08K 3/04* (2013.01); *C08K 7/18* (2013.01); *C08L 61/16* (2013.01); *C08L 63/00* (2013.01); *C08L 91/06*

(56) References Cited

OTHER PUBLICATIONS

International Search Report dated May 20, 2014, issued for PCT/JP2014/054137.
Office Action dated Aug. 26, 2014, issued for the Japanese Patent Application No. 2014-152874.
Office Action dated May 23, 2017, issued for the Taiwanese patent application No. 103110201.

* cited by examiner

[Fig.1]
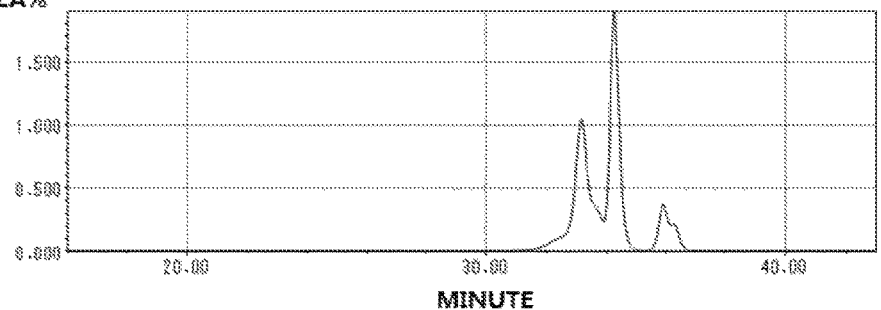
[Fig.2]
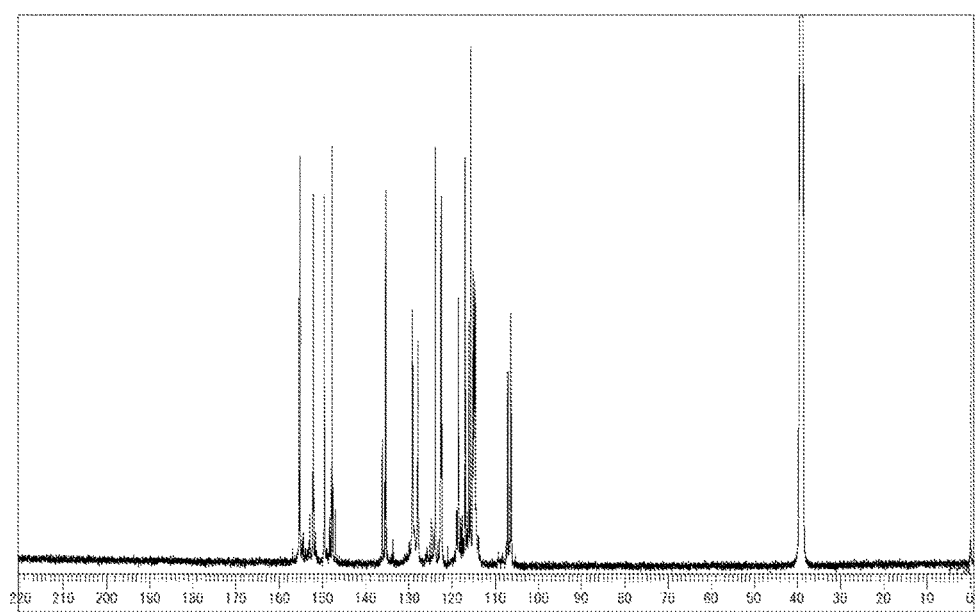

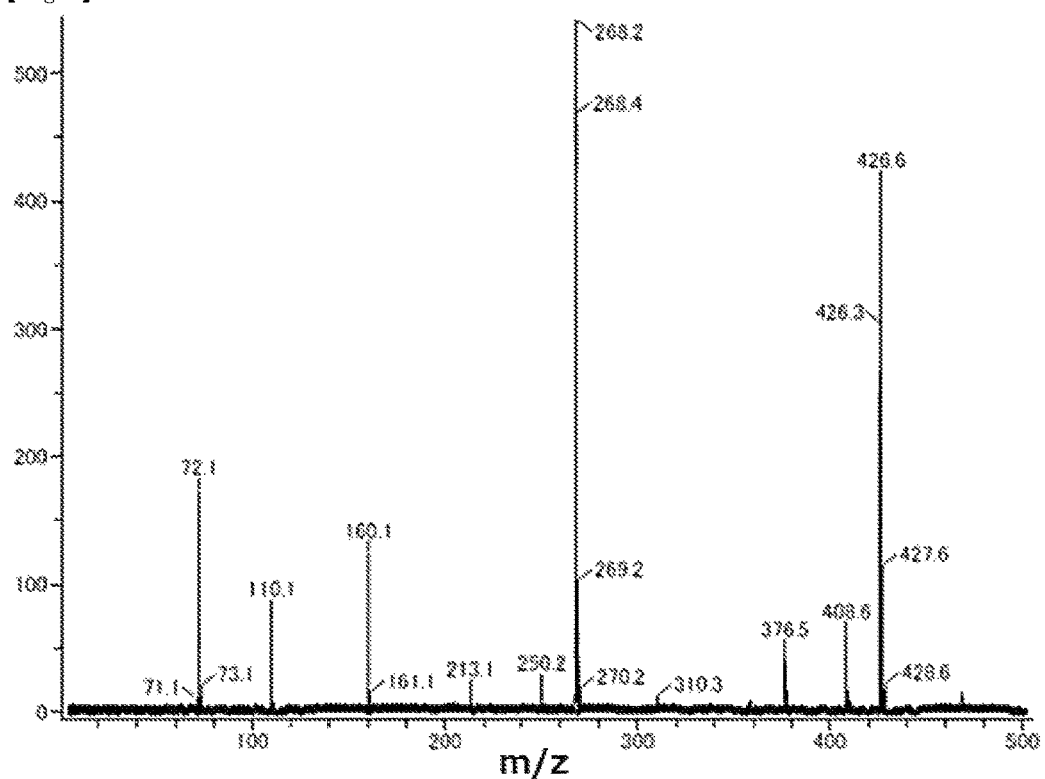

[Fig.4]
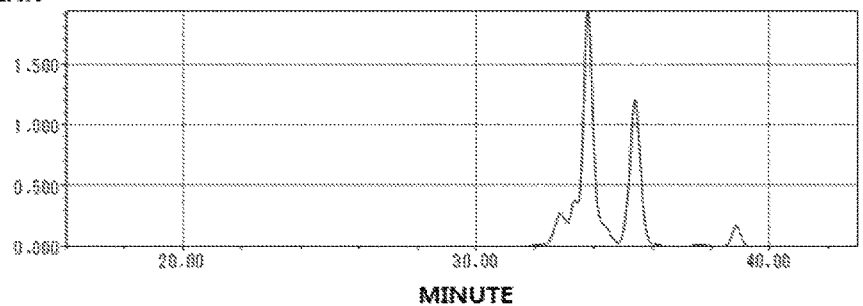
[Fig.5]
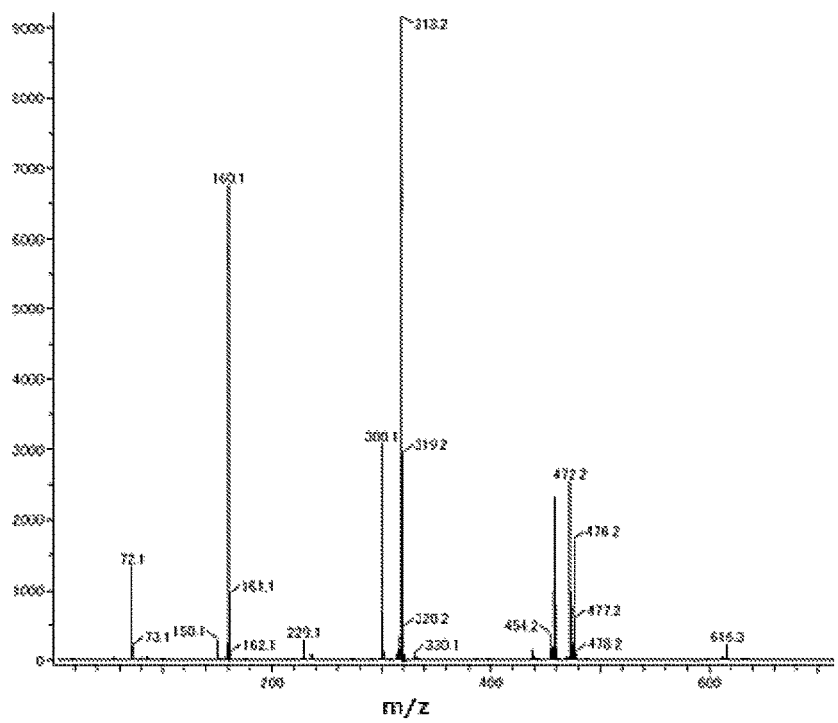

COMPOUND CONTAINING PHENOLIC HYDROXYL GROUP, PHENOLIC RESIN, CURABLE COMPOSITION, CURED PRODUCT THEREOF, SEMICONDUCTOR SEALING MATERIAL, AND PRINTED CIRCUIT BOARD

CROSS REFERENCE TO RELATED APPLICATIONS

This application is related to co-pending application: "COMPOUND CONTAINING PHENOLIC HYDROXYL GROUP, PHENOLIC RESIN, CURABLE COMPOSITION, CURED PRODUCT THEREOF, SEMICONDUCTOR SEALING MATERIAL, AND PRINTED CIRCUIT BOARD" filed even date herewith in the names of Yutaka Satou and Ayumi Takahashi as a national phase entry of PCT/JP2014/054141, which application is assigned to the assignee of the present application and is incorporated by reference herein.

TECHNICAL FIELD

The present invention relates to a compound containing a phenolic hydroxyl group which exhibits excellent heat resistance and flame retardancy in terms of a cured product thereof, a phenolic resin including the same, a curable composition and a cured product thereof, a semiconductor sealing material, and a printed circuit board.

BACKGROUND ART

A phenolic resin has been used, for example, as a curing agent for epoxy resins, and an epoxy resin composition which is cured by a phenolic resin as a curing agent is widely used in electrical and electronic fields such as a semiconductor sealing material and a printed circuit board insulating material from the viewpoint that the cured product has excellent heat resistance and moisture resistance, in addition to an adhesive, a molding material, and a coating material.

Among these, a power semiconductor represented by a power module for an automobile is a technology crucial to energy saving in electrical and electronic equipment, and with a larger current, miniaturization, and high efficiency of a power semiconductor, transition from a silicon (Si) semiconductor in the related art to a silicon carbide (SiC) semiconductor has been advancing. The advantage of the SiC semiconductor is that the SiC semiconductor can be operated under higher temperature conditions, and therefore, a semiconductor sealing material is required to have higher heat resistance than those of semiconductor sealing materials in the related art. In addition, it is also important for the required performance of a semiconductor sealing resin to exhibit high flame retardancy without using a halogen-based flame retardant, and a resin material which has such performance has been required.

As the resin material to cope with these various required characteristics, for example, the compound containing a phenolic hydroxyl group represented by the following structural formula is known (refer to PTL 1).

[Chem. 1]

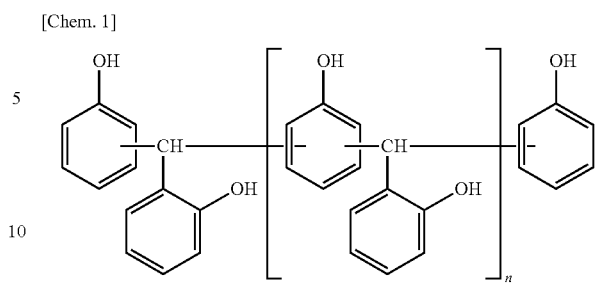

Such a compound containing a phenolic hydroxyl group exhibits extremely excellent heat resistance in terms of a cured product thereof; however, does not have sufficient flame retardancy.

CITATION LIST

Patent Literature

[PTL 1] JP-A-2002-114889

SUMMARY OF INVENTION

Technical Problem

Therefore, an object of the present invention is to provide a compound containing a phenolic hydroxyl group, which exhibits excellent heat resistance and flame retardancy in terms of a cured product thereof, a phenolic resin including the same, a curable composition and a cured product thereof, a semiconductor sealing material, and a printed circuit board.

Solution to Problem

As a result of thorough studies in order to achieve the above object, the present inventors found that, since a reaction product of a compound having a quinone skeleton and a compound having a naphthol or dihydroxynaphthalene skeleton has a molecular structure having a high hydroxyl group concentration, in which aromatic nuclei are mutually bonded not through a methylene chain, and the reactivity of the hydroxyl group is high, a reaction product exhibits excellent heat resistance and flame retardancy in terms of a cured product thereof, and completed the present invention.

That is, the present invention relates to a compound containing a phenolic hydroxyl group which has a molecular structure represented by the following General Formula (I):

[Chem. 2]

in the formula, X is a structural site represented by the following Structural Formula (x1) or (x2);

[Chem. 3]

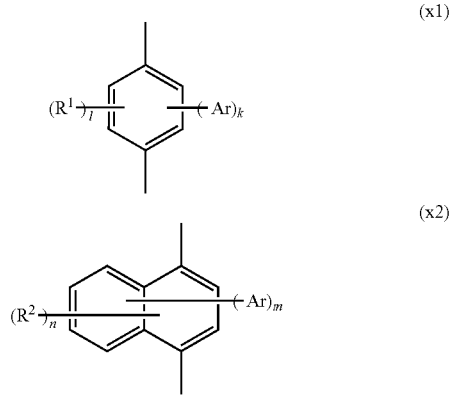

in Formula (x1) or (x2), each of $R^1$ and $R^2$ is any one of an alkyl group having 1 to 4 carbon atoms, an alkoxy group having 1 to 4 carbon atoms, an aryl group, and an aralkyl group, l is an integer of 0 to 3, n is an integer of 0 to 4, in a case where l or n is 2 or greater, a plurality of $R^1$'s or $R^2$'s may be the same as or different from each other, k is an integer of 1 to 3, m is 1 or 2, Ar is a structural site represented by the following Structural Formula (Ar1), and in a case where k or m is 2 or greater, a plurality of Ar's may be the same as or different from each other;

[Chem. 4]

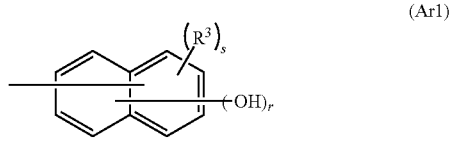

in the formula, $R^3$ is any one of an alkyl group having 1 to 4 carbon atoms, an alkoxy group having 1 to 4 carbon atoms, an aryl group, and an aralkyl group, $R^3$ may be bonded to either of two aromatic nuclei, s is an integer of 0 to 6, in a case where s is 2 or greater, a plurality of $R^3$'s may be the same as or different from each other, and r is 1 or 2.

The present invention further relates to a phenolic resin containing the compound containing a phenolic hydroxyl group.

The present invention still further relates to a preparation method of a phenolic resin, including reacting a compound (Q) having a quinone structure in the molecular structure and a compound (P) having a naphthol or dihydroxynaphthalene skeleton with each other.

The present invention still further relates to a phenolic resin prepared by the preparation method.

The present invention still further relates to a curable composition including the compound containing a phenolic hydroxyl group or the phenolic resin and a curing agent, as essential components.

The present invention still further relates to a cured product which is obtained by a curing reaction of the curable composition.

The present invention still further relates to a semiconductor sealing material containing the curable composition and an inorganic filler.

The present invention still further relates to a printed circuit board obtained by impregnating a reinforcement basic material with a resin composition varnished by blending the curable composition with an organic solvent, and superposing a copper foil on the resulting material, followed by heat-pressing.

Advantageous Effects of Invention

According to the present invention, it is possible to provide a compound containing a phenolic hydroxyl group which has a low melt viscosity, and exhibits excellent heat resistance and flame retardancy in terms of a cured product thereof, a phenolic resin including the same, a curable composition and a cured product thereof, a semiconductor sealing material, and a printed circuit board.

BRIEF DESCRIPTION OF DRAWINGS

FIG. 1 is a GPC chart of a phenolic resin (1) obtained in Example 1.
FIG. 2 is a 13C-NMR chart of the phenolic resin (1) obtained in Example 1.
FIG. 3 is an MS spectrum of the phenolic resin (1) obtained in Example 1.
FIG. 4 is a GPC chart of a phenolic resin (2) obtained in Example 2.
FIG. 5 is an MS spectrum of the phenolic resin (2) obtained in Example 2.

DESCRIPTION OF EMBODIMENTS

Hereinafter, the present invention will be described in detail.

The compound containing a phenolic hydroxyl group of the present invention has a molecular structure represented by the following General Formula (I):

[Chem. 5]

in the formula, X is a structural site represented by the following Structural Formula (x1) or (x2);

[Chem. 6]

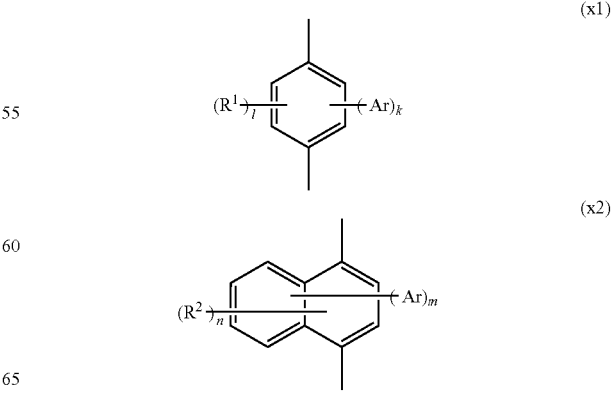

in Formula (x1) or (x2), each of $R^1$ and $R^2$ is any one of an alkyl group having 1 to 4 carbon atoms, an alkoxy group having 1 to 4 carbon atoms, an aryl group, and an aralkyl group, l is an integer of 0 to 3, n is an integer of 0 to 4, in a case where l or n is 2 or greater, a plurality of $R^1$'s or $R^2$'s may be the same as or different from each other, k is an integer of 1 to 3, m is 1 or 2, Ar is a structural site represented by the following Structural Formula (Ar1), and in a case where k or m is 2 or greater, a plurality of Ar's may be the same as or different from each other;

[Chem. 7]

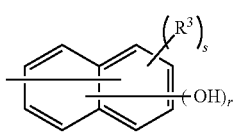

(Ar1)

in the formula, $R^3$ is any one of an alkyl group having 1 to 4 carbon atoms, an alkoxy group having 1 to 4 carbon atoms, an aryl group, and an aralkyl group, $R^3$ may be bonded to either of two aromatic nuclei, and s is an integer of 0 to 6, in a case where s is 2 or greater, a plurality of $R^3$'s may be the same as or different from each other, and r is 1 or 2.

The compound containing a phenolic hydroxyl group of the present invention represented by General Formula (I) has a low molecular weight, and a high aromatic ring concentration and a high hydroxyl group concentration since the compound containing a phenolic hydroxyl group has a structure in which aromatic nuclei are mutually boned not through a methylene chain. Such a compound tends to be decreased in flame retardancy since, the concentration of a hydroxyl group having flammability is increased, and a large number of reactive groups exist in close proximity, while it exhibits excellent heat resistance in terms of a cured product thereof. In contrast, the compound containing a phenolic hydroxyl group of the present invention exhibits both excellent heat resistance and flame retardancy in terms of a cured product thereof since the compound containing a phenolic hydroxyl group has a biphenyl skeleton or a terphenyl skeleton, and in Structural Formula (x1) or (x2), two hydroxyl groups positioned at the para position of the aromatic nucleus have excellent reactivity.

As the compound represented by General Formula (I), a compound prepared by a method in which a compound (Q) having a quinone structure in the molecular structure and a compound (P) having a naphthol or dihydroxynaphthalene skeleton are reacted at a temperature range of 40° C. to 180° C. under non-catalytic or acid catalytic conditions is exemplified. In the case of preparing the compound containing a phenolic hydroxyl group of the present invention by such a method, it is possible to selectively prepare an arbitrary component according to the reaction conditions, or it is possible to prepare a phenolic resin which is a mixture of a plurality of compounds containing a phenolic hydroxyl group. In addition, only the arbitrary component is isolated from the phenolic resin which is a mixture and may be used.

As the compound (Q) having a quinone structure in the molecular structure, the compound represented by the following Structural Formula (Q1) or (Q2) is exemplified.

[Chem. 8]

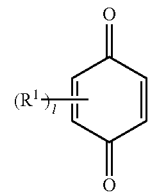

(Q1)

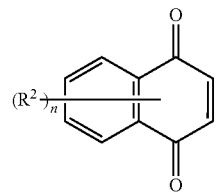

(Q2)

In Formula (Q1) or (Q2), each of $R^1$ and $R^2$ is any one of an alkyl group having 1 to 4 carbon atoms, an alkoxy group having 1 to 4 carbon atoms, an aryl group, and an aralkyl group, l is an integer of 0 to 3, and n is an integer of 0 to 4, and in a case where l or n is 2 or greater, a plurality of $R^1$'s or $R^2$'s may be the same as or different from each other.

Specifically, parabenzoquinone, 2-methyl benzoquinone, 2,3,5-trimethyl-benzoquinone, and naphthoquinone are exemplified. These may be used alone respectively, or two or more kinds may be used in combination.

As the compound (P) having a naphthol or dihydroxynaphthalene skeleton in the molecular structure, for example, the compound represented by the following Structural Formula (P1) is exemplified.

[Chem. 9]

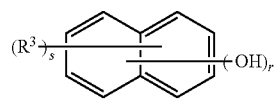

(P1)

In Formula (P1), $R^3$ is any one of an alkyl group having 1 to 4 carbon atoms, an alkoxy group having 1 to 4 carbon atoms, an aryl group, and an aralkyl group, and s is an integer of 0 to 6, in a case where s is 2 or greater, a plurality of $R^3$'s may be the same as or different from each other, and r is 1 or 2, respectively.

Specifically, 1-naphthol, 2-naphthol, 1,4-dihydroxynaphthalene, 1,5-dihydroxynaphthalene, 1,6-dihydroxynaphthalene, 2,6-dihydroxynaphthalene, and 2,7-dihydroxynaphthalene are exemplified. These may be used alone respectively, or two or more kinds may be used in combination.

Among these, since heat resistance and flame retardancy in terms of a cured product thereof are excellent, a compound having a dihydroxynaphthalene skeleton in which r is 2 in Structural Formula (P1) is preferable, 1,5-dihydroxynaphthalene, 1,6-dihydroxynaphthalene, or 2,7-dihydroxynaphthalene is more preferable, and 2,7-dihydroxynaphthalene is particularly preferable.

Since the reactivity of the reaction of the compound (Q) having a quinone structure in the molecular structure with the compound (P) having a naphthol or dihydroxynaphthalene skeleton is high, the reaction proceeds even under non-catalytic conditions; however, the reaction may be performed by using a suitable acid catalyst. Examples of the acid catalyst used here include inorganic acids such as hydrochloric acid, sulfuric acid, and phosphoric acid, organic acids such as methanesulfonic acid, p-toluenesulfonic acid, and oxalic acid, or Lewis acids such as boron trifluoride, anhydrous aluminum chloride, and zinc chloride. In the case of using one of the acid catalysts described above, the acid catalyst is preferably used in the amount of 5.0% by mass or less with respect to the total mass of the compound (Q) having a quinone structure and the compound (P) having a naphthol or dihydroxynaphthalene skeleton.

In addition, the reaction is preferably performed under solvent-free conditions; however, the reaction may be performed in an organic solvent, as necessary. Examples of the organic solvent used here include methyl cellosolve, isopropyl alcohol, ethyl cellosolve, toluene, xylene, and methyl isobutyl ketone. In the case of using one of the organic solvents described above, the organic solvent is preferably used in a proportion within a range of 50 parts by mass to 200 parts by mass with respect to the total 100 parts by mass of the compound (Q) having a quinone structure and the compound (P) having a naphthol or dihydroxynaphthalene skeleton, from the viewpoint of improvement of reaction efficiency.

After the reaction of the compound (Q) having a quinone structure in the molecular structure with the compound (P) having a naphthol or dihydroxynaphthalene skeleton ends, drying under reduced pressure is performed, whereby a desired compound containing a phenolic hydroxyl group or phenolic resin can be obtained.

The compound containing a phenolic hydroxyl group of the present invention exhibits the effects of the present invention in which heat resistance and flame retardancy in terms of a cured product thereof are excellent as long as the compound has the structure represented by General Formula (I). Hereinafter, more preferable compounds containing a phenolic hydroxyl group having the structure represented by General Formula (I) will be described in detail.

As a representative compound containing a phenolic hydroxyl group represented by the following General Formula (I), the compound containing a phenolic hydroxyl group represented by any one of the following General Formulas (I-1) to (I-3) is exemplified.

[Chem. 10]

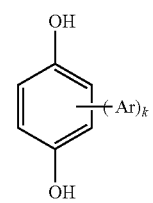
(I-1)

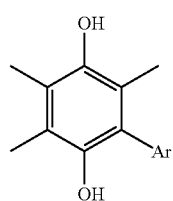
(I-2)

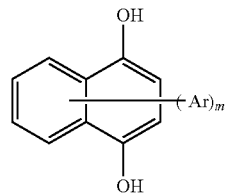
(I-3)

In Formulas (I-1) to (I-3), k is an integer of 1 to 3, m is 1 or 2, and Ar is a structural site represented by the following Structural Formula (Ar1), and in a case where k or m is 2 or greater, a plurality of Ar's may be the same as or different from each other.

[Chem. 11]

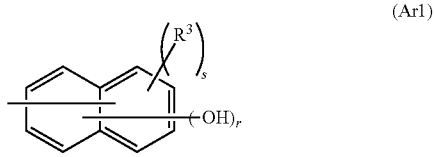
(Ar1)

In the formula, $R^3$ is any one of an alkyl group having 1 to 4 carbon atoms, an alkoxy group having 1 to 4 carbon atoms, an aryl group, and an aralkyl group, $R^3$ may be bonded to either of two aromatic nuclei, s is an integer of 0 to 6, in a case where s is 2 or greater, a plurality of $R^3$'s may be the same as or different from each other, and r is 1 or 2.

As the compound containing a phenolic hydroxyl group represented by Structural Formula (I-1), more specifically, the compound represented by the following Structural Formula (1) or (2) is exemplified.

[Chem. 12]

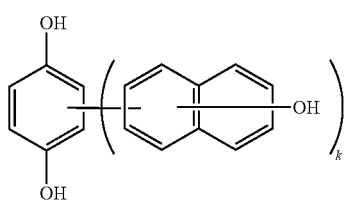
(1)

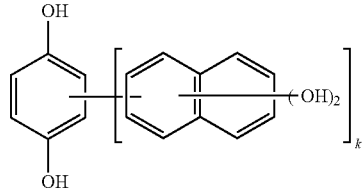
(2)

In Formula (1) or (2), k is an integer of 1 to 3.

The compound containing a phenolic hydroxyl group represented by Structural Formula (1) can be prepared by the method described above, for example, using parabenzoquinone as the compound (Q) having a quinone structure in the molecular structure and naphthol as the compound (P) having a naphthol or dihydroxynaphthalene skeleton. At this time, since a phenolic resin which has low melt viscosity and exhibits more excellent heat resistance and flame retardancy in terms of a cured product thereof is obtained, the reaction proportion between parabenzoquinone and naphthol is preferably a proportion in which naphthol is within a range of 0.1 moles to 10.0 moles with respect to 1 mole of parabenzoquinone.

Among the compounds containing a phenolic hydroxyl group represented by Structural Formula (1), since heat resistance and flame retardancy in terms of a cured product thereof are particularly excellent, a phenolic resin containing a binuclear compound (x1) having the k value of 1 in Structural Formula (1) and a trinuclear compound (x2) having the k value of 2 in Structural Formula (1) is preferably used, and it is more preferable that the content of the binuclear compound (x1) in the phenolic resin is within a range of 10% to 70% in area ratio in a GPC measurement, and the content of the trinuclear compound (x2) is within a range of 10% to 50% in area ratio in a GPC measurement.

Moreover, in the present invention, the content of the binuclear compound (x1), the trinuclear compound (x2), and other components in a phenolic resin refers to a proportion of the peak area of each component with respect to the total peak area of the phenolic resin, which is calculated from GPC measurement data under the following conditions.

<GPC Measurement Conditions>
Measurement apparatus: "HLC-8220 GPC" manufactured by Tosoh Corporation Column: guard column "HXL-L" manufactured by Tosoh Corporation +
"TSK-GEL G2000HXL" manufactured by Tosoh Corporation +
"TSK-GEL G2000HXL" manufactured by Tosoh Corporation +
"TSK-GEL G3000HXL" manufactured by Tosoh Corporation +
"TSK-GEL G4000HXL" manufactured by Tosoh Corporation Detector: RI (differential refractometer)
Data processing: "GPC-8020 model II Version 4.10" manufactured by Tosoh Corporation
Measurement conditions:

| column temperature | 40° C. |
| eluent | tetrahydrofuran |
| flow rate | 1.0 ml/min |

Standard: according to the measurement manual of the "GPC-8020 model II Version 4.10", the following monodisperse polystyrene of which the molecular weight is known is used.
(Polystyrene Used)
"A-500" manufactured by Tosoh Corporation
"A-1000" manufactured by Tosoh Corporation
"A-2500" manufactured by Tosoh Corporation
"A-5000" manufactured by Tosoh Corporation
"F-1" manufactured by Tosoh Corporation
"F-2" manufactured by Tosoh Corporation
"F-4" manufactured by Tosoh Corporation
"F-10" manufactured by Tosoh Corporation
"F-20" manufactured by Tosoh Corporation
"F-40" manufactured by Tosoh Corporation
"F-80" manufactured by Tosoh Corporation
"F-128" manufactured by Tosoh Corporation
Sample: a solution (50 μl) obtained by filtering a tetrahydrofuran solution of 1.0% by mass in terms of the resin solid content through a microfilter.

As the compound represented by Structural Formula (1), a compound represented by any one of the following Structural Formulas (1-1) to (1-10) is exemplified.

[Chem. 13]

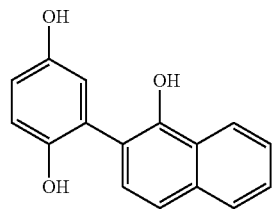
(1-1)

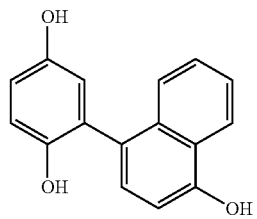
(1-2)

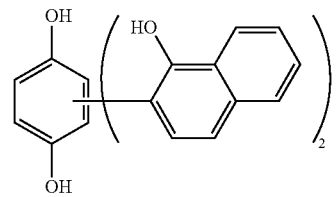
(1-3)

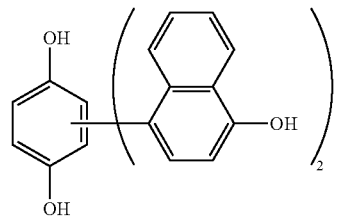
(1-4)

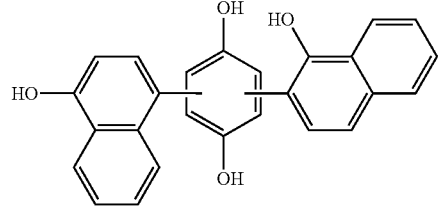
(1-5)

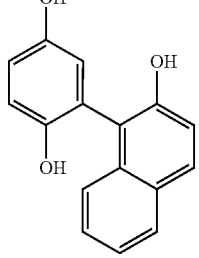
(1-6)

(1-7)

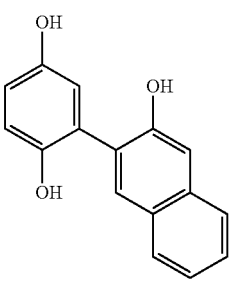

(1-8)

(1-9)

(1-10)

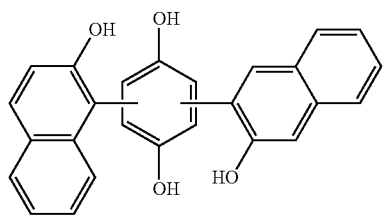

Among the compounds containing a phenolic hydroxyl group represented by General Formula (I), in particular, the compound containing a phenolic hydroxyl group represented by Structural Formula (2) exhibits particularly excellent heat resistance and flame retardancy in terms of a cured product thereof.

Among these, since heat resistance and flame retardancy of the cured product are more excellent, a phenolic resin containing a binuclear compound (x1) having the k value of 1 in Structural Formula (2) and a trinuclear compound (x2) having the k value of 2 in Structural Formula (2) is preferably used, and it is more preferable that the content of the binuclear compound (x1) in the phenolic resin is within a range of 10% to 70% in area ratio in a GPC measurement, and the content of the trinuclear compound (x2) is within a range of 10% to 50% in area ratio in a GPC measurement.

The compound containing a phenolic hydroxyl group represented by Structural Formula (2) can be prepared by the method described above, for example, using parabenzoquinone as the compound (Q) having a quinone structure in the molecular structure and dihydroxynaphthalene as the compound (P) having a naphthol or dihydroxynaphthalene skeleton. At this time, since a phenolic resin which exhibits more excellent heat resistance and flame retardancy in terms of a cured product thereof is obtained, the reaction proportion between parabenzoquinone and dihydroxynaphthalene is preferably a proportion in which dihydroxynaphthalene is within a range of 0.1 moles to 10.0 moles with respect to 1 mole of parabenzoquinone.

The dihydroxynaphthalene used here may be any regioisomer of 1,4-dihydroxynaphthalene, 1,5-dihydroxynaphthalene, 1,6-dihydroxynaphthalene, 2,6-dihydroxynaphthalene, and 2,7-dihydroxynaphthalene. Among these, 2,7-dihydroxynaphthalene is preferable since a phenolic resin which has low melt viscosity and exhibits excellent heat resistance and flame retardancy in terms of a cured product thereof is obtained.

As the compound represented by Structural Formula (2), a compound represented by any one of the following Structural Formulas (2-1) to (2-24) is exemplified.

[Chem. 14]

(2-1)

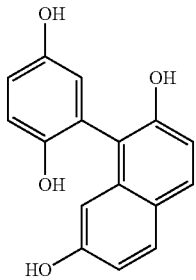

(2-2)

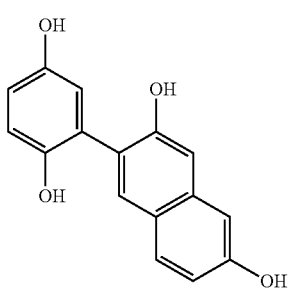

(2-3)

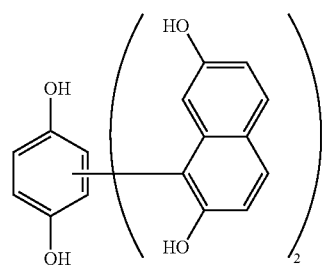

(2-4)

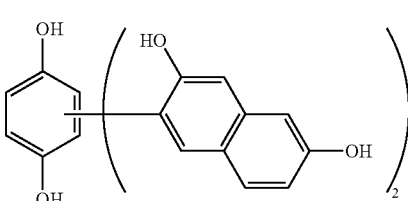

(2-5)

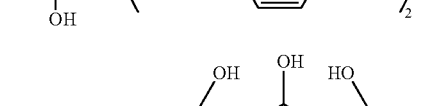
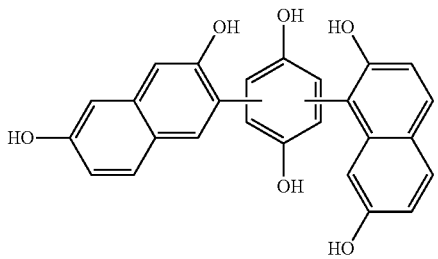

-continued (2-6)
(2-7)
(2-8)
(2-9)
(2-10)
(2-11)
(2-12)
(2-13)
(2-14)
(2-15)
(2-16)
(2-17)
(2-18)

-continued (2-19)
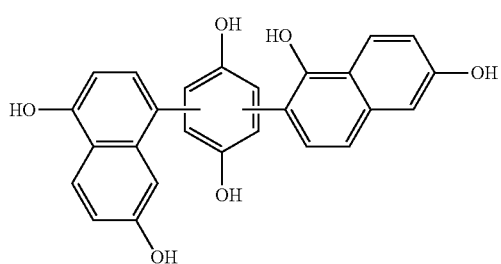

(2-20)
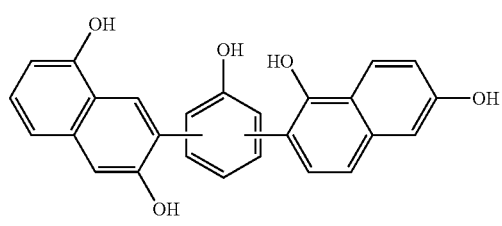

(2-21)
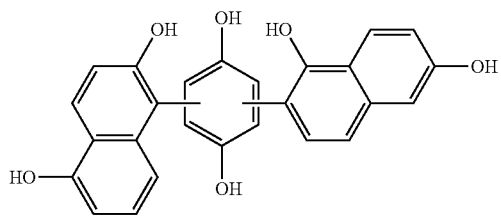

(2-22)
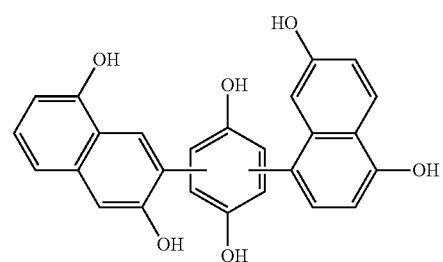

(2-23)
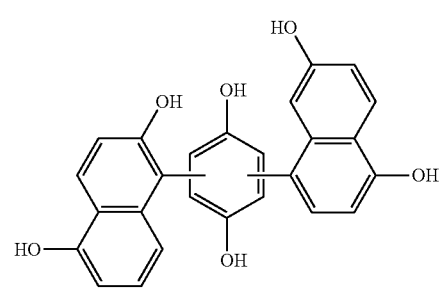

(2-24)
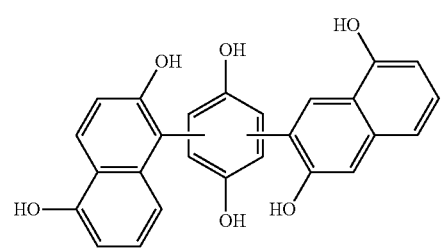

As the compound containing a phenolic hydroxyl group represented by Structural Formula (I-2), more specifically, the compound containing a phenolic hydroxyl group represented by the following Structural Formula (3) is exemplified.

[Chem. 17]

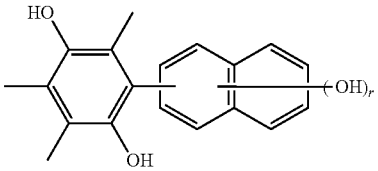

(3)

In Formula (3), r is 1 or 2.

The compound containing a phenolic hydroxyl group represented by Structural Formula (3) can be prepared by the method described above, for example, using 2,4,6-trimethyl-parabenzoquinone as the compound (Q) having a quinone structure in the molecular structure and naphthol or dihydroxynaphthalene as the compound (P) having a naphthol or dihydroxynaphthalene skeleton. At this time, since a phenolic resin which has low melt viscosity and exhibits more excellent heat resistance and flame retardancy in terms of a cured product thereof is obtained, the reaction proportion between 2,4,6-trimethyl-parabenzoquinone and the compound (P) having a naphthol or dihydroxynaphthalene skeleton is preferably a proportion in which the compound (P) having a naphthol or dihydroxynaphthalene skeleton is within a range of 0.1 moles to 10.0 moles with respect to 1 mole of 2,4,6-trimethyl-parabenzoquinone.

As the compound represented by Structural Formula (3), a compound represented by any one of the following Structural Formulas (3-1) to (3-12) is exemplified.

[Chem. 18]

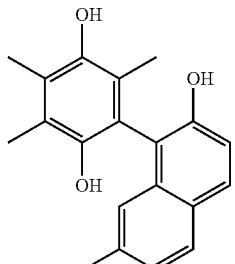

(3-1)

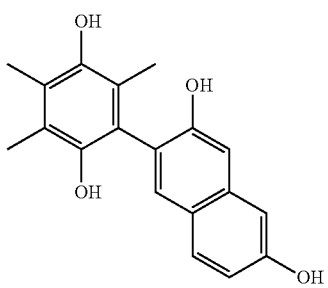

(3-2)

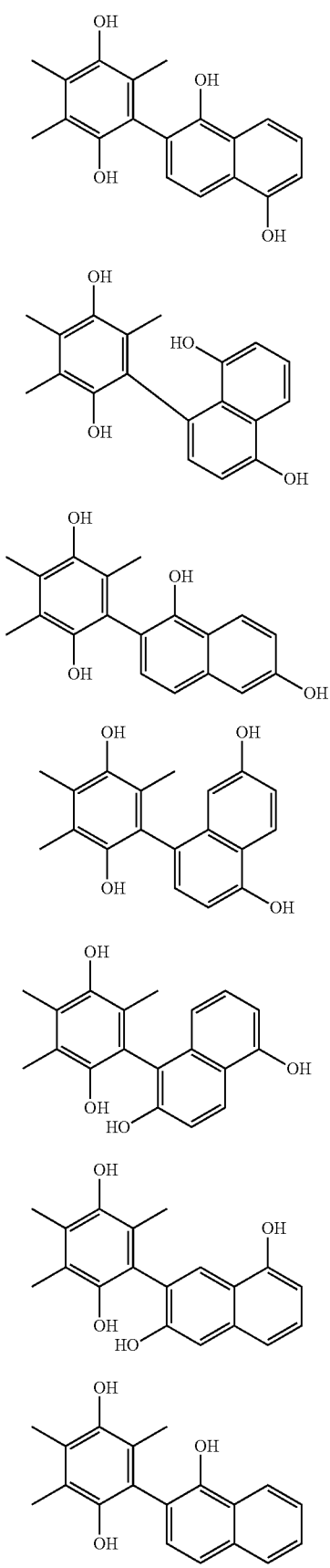

(3-3)
(3-4)
(3-5)
(3-6)
(3-7)
(3-8)
(3-9)

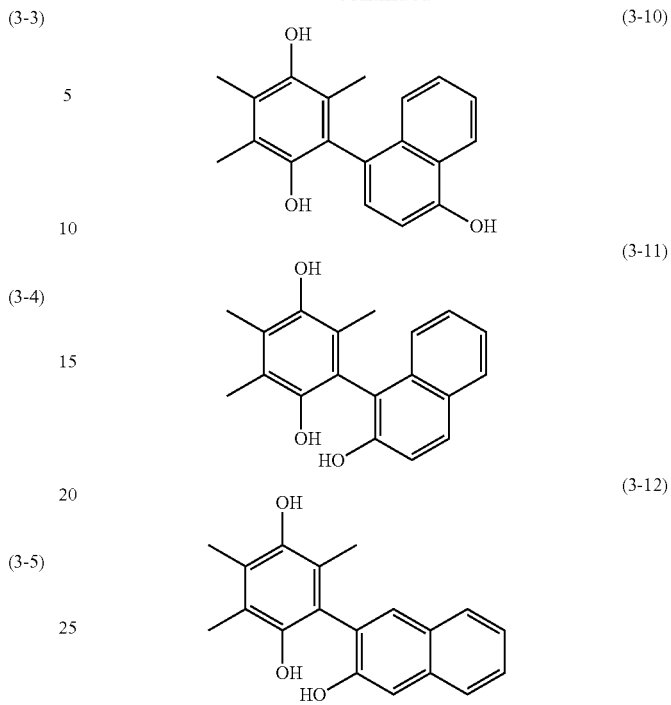

(3-10)
(3-11)
(3-12)

As the compound containing a phenolic hydroxyl group represented by Structural Formula (I-3), more specifically, the compound containing a phenolic hydroxyl group represented by any one of the following Structural Formulas (4) and (5) is exemplified.

[Chem. 19]

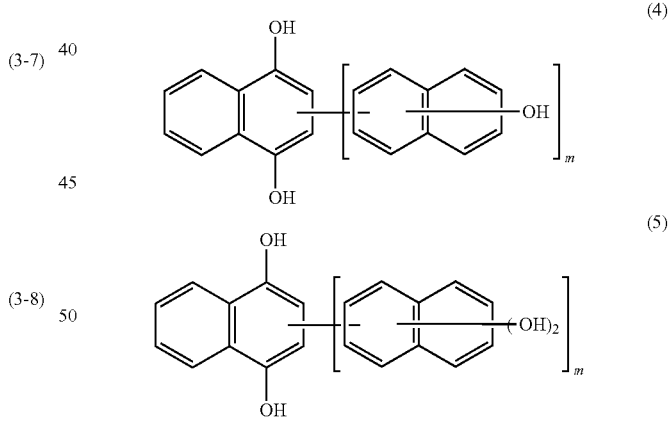

(4)
(5)

In Formula (4) or (5), m is 1 or 2.

The compound containing a phenolic hydroxyl group represented by Structural Formula (4) can be prepared by the method described above, for example, using naphthoquinone as the compound (Q) having a quinone structure in the molecular structure and naphthol as the compound (P) having a naphthol or dihydroxynaphthalene skeleton. At this time, since a phenolic resin which has low melt viscosity and exhibits more excellent heat resistance and flame retardancy in terms of a cured product thereof is obtained, the reaction proportion between naphthoquinone and naphthol is preferably a proportion in which the compound (P) having a naphthol or dihydroxynaphthalene skeleton is within a range of 0.1 moles to 10.0 moles with respect to 1 mole of naphthoquinone.

As the compound represented by Structural Formula (4), an epoxy compound represented by any one of the following Structural Formulas (4-1) to (4-4) is exemplified.

[Chem. 20]

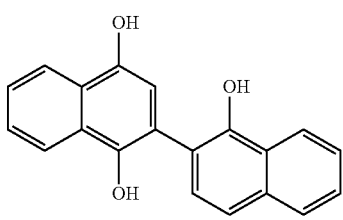
(4-1)

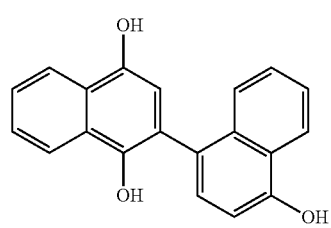
(4-2)

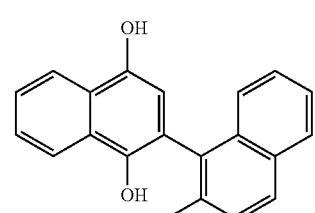
(4-3)

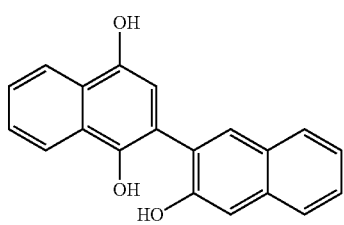
(4-4)

Among the compounds containing a phenolic hydroxyl group represented by General Formula (I), in particular, the compound containing a phenolic hydroxyl group represented by Structural Formula (5) exhibits particularly excellent heat resistance and flame retardancy in terms of a cured product thereof.

Among these, since the melt viscosity is low, and heat resistance and flame retardancy in terms of a cured product thereof are more excellent, a phenolic resin containing a binuclear compound (x1) having the k value of 1 in Structural Formula (5) as an essential component is preferably used, and the content of the binuclear compound (x1) in the phenolic resin is preferably within a range of 5% to 70% in area ratio in a GPC measurement.

The compound containing a phenolic hydroxyl group represented by Structural Formula (5) can be prepared by the method described above, for example, using naphthoquinone as the compound (Q) having a quinone structure in the molecular structure and dihydroxynaphthalene as the compound (P) having a naphthol or dihydroxynaphthalene skeleton. At this time, since a phenolic resin which exhibits more excellent heat resistance and flame retardancy in terms of a cured product thereof is obtained, the reaction proportion between naphthoquinone and dihydroxynaphthalene is preferably a proportion in which dihydroxynaphthalene is within a range of 0.1 moles to 10.0 moles with respect to 1 mole of naphthoquinone.

The dihydroxynaphthalene used here may be any one of 1,4-dihydroxynaphthalene, 1,5-dihydroxynaphthalene, 1,6-dihydroxynaphthalene, 2,6-dihydroxynaphthalene, and 2,7-dihydroxynaphthalene Among these, 2,7-dihydroxynaphthalene is preferable since a phenolic resin which exhibits excellent heat resistance and flame retardancy in terms of a cured product thereof is obtained.

As the compound represented by Structural Formula (5), the following Structural Formulas (5-1) to (5-8) are exemplified.

[Chem. 21]

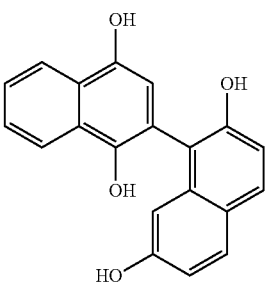
(5-1)

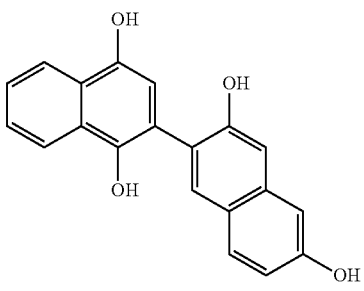
(5-2)

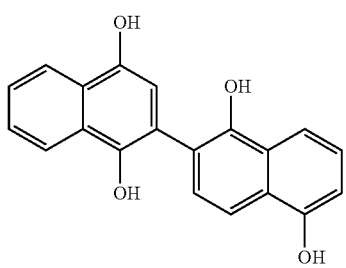
(5-3)

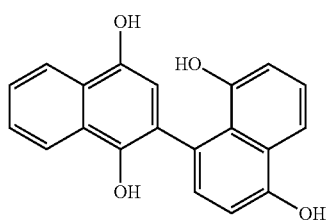
(5-4)

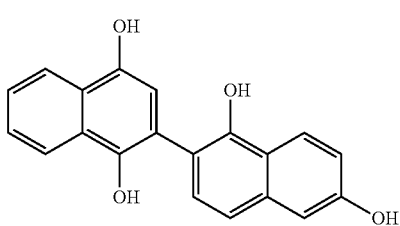
(5-5)

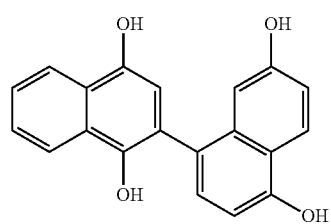
(5-6)

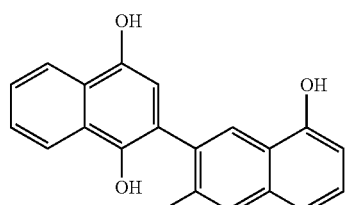
(5-7)

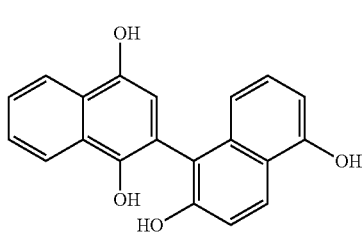
(5-8)

A phenolic resin containing the compound containing a phenolic hydroxyl group represented by Structural Formula (5) may further contain a compound containing a phenolic hydroxyl group other than these. Among these, since flame retardancy in terms of a cured product thereof is excellent, the dinaphthofuran compound represented by the following Structural Formula (5') is preferably contained.

[Chem. 22]

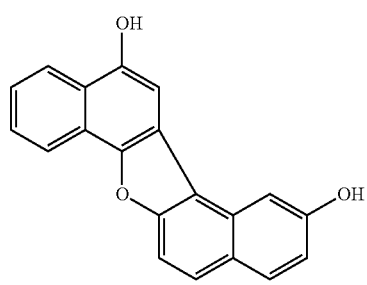
(5')

In this case, as the content proportion of each component in the phenolic resin, it is preferable that the content of the binuclear compound (x1) having the m value of 1 in Structural Formula (5) is within a range of 5% to 70% in area ratio in a GPC measurement, and the content of the dinaphthofuran compound is within a range of 1% to 60%.

Among the compounds containing a phenolic hydroxyl group of the present invention exemplified above, the compound containing a phenolic hydroxyl group represented by Structural Formula (2) or (5) is preferable from the viewpoint of excellent balance between the melt viscosity and heat resistance and flame retardancy in terms of a cured product thereof, and the compound containing a phenolic hydroxyl group represented by Structural Formula (5) is more preferable since heat resistance and flame retardancy in terms of a cured product thereof are more excellent.

In a phenolic resin including the compound containing a phenolic hydroxyl group of the present invention, the hydroxyl equivalent is preferably within a range of 60 g/eq to 150 g/eq from the viewpoint of excellent curing properties. In addition, the softening point is preferably within a range of 80° C. to 150° C.

The curable composition of the present invention contains the compound containing a phenolic hydroxyl group described above or a phenolic resin including the same, and a curing agent as essential components. As the curing agent, an epoxy resin is exemplified.

Specific examples of the epoxy resin used here include naphthalene skeleton-containing epoxy resins such as 1,6-diglycidyloxy naphthalene, 2,7-diglycidyloxy naphthalene, an α-naphthol novolak type epoxy resin, a β-naphthol novolak type epoxy resin, polyglycidyl ether of α-naphthol/β-naphthol co-condensed novolak, a naphthol aralkyl type epoxy resin, and 1,1-bis(2,7-diglycidyloxy-1-naphthyl)alkane; bisphenol type epoxy resins such as a bisphenol A type epoxy resin and a bisphenol F type epoxy resin; biphenyl type epoxy resins such as a biphenyl type epoxy resin and a tetramethyl biphenyl type epoxy resin; novolak type epoxy resins such as a phenol novolak type epoxy resin, a cresol novolak type epoxy resin, a bisphenol A novolak type epoxy resin, a bisphenol F novolak type epoxy resin, an epoxidized product of a condensate of a phenol-based compound and an aromatic aldehyde having a phenolic hydroxyl group, and a biphenyl novolak type epoxy resin; triphenylmethane type epoxy resins; tetraphenyl ethane type epoxy resins; dicyclopentadiene-phenol addition reaction type epoxy resins; phenol aralkyl type epoxy resins; phosphorus atom-containing epoxy resins; and modified epoxy resins of the present invention.

In the case of using an epoxy resin as a curing agent, the blending proportion between the compound containing a phenolic hydroxyl group or the phenolic resin and the epoxy resin is preferably a proportion in which the equivalent ratio (phenolic hydroxyl group/epoxy group) of the phenolic hydroxyl group in the compound containing a phenolic hydroxyl group or the phenolic resin to the epoxy group in the epoxy resin is 1/0.5 to 1/1.5 since reactivity and heat resistance in terms of a cured product thereof are excellent at this proportion.

In addition, in the case of using an epoxy resin as a curing agent, in addition to the compound containing a phenolic hydroxyl group or the phenolic resin of the present invention, other curing agents for epoxy resin may be used in combination. As other curing agents for epoxy resin, various known curing agents such as an amine-based compound, an amide-based compound, an acid anhydride-based compound, and a phenol-based compound are exemplified. Specifically, examples of the amine-based compound include diaminodiphenyl methane, diethylenetriamine, triethylenetetramine, diaminodiphenyl sulfone, isophoronediamine, imidazole, BF$_3$-amine complex, and guanidine derivatives, examples of the amide-based compound include dicyandiamide and a polyamide resin synthesized from a linolenic acid dimer and ethylenediamine, examples of the acid anhydride-based compound include phthalic anhydride, trimellitic anhydride, pyromellitic anhydride, maleic anhydride, tetrahydrophthalic anhydride, methyl tetrahydrophthalic anhydride, methylnadic anhydride, hexahydrophthalic anhydride, and methylhexahydrophthalic anhydride, and examples of the phenol-based compound include polyvalent phenolic compounds such as a phenol novolak resin, a cresol novolak resin, an aromatic hydrocarbon formaldehyde resin-modified phenolic resin, a dicyclopentadiene phenol adduct type resin, a phenol aralkyl resin (Xylok resin), a naphthol aralkyl resin, a triphenylol methane resin, a tetraphenylol ethane resin, a naphthol novolak resin, a naphthol-phenol co-condensed novolak resin, a naphthol-cresol co-condensed novolak resin, a biphenyl-modified phenolic resin (polyvalent phenolic compound in which a phenolic nucleus is linked by a bismethylene group), a biphenyl-modified naphthol resin (polyvalent naphthol compound in which a phenolic nucleus is linked by a bismethylene group), an aminotriazine-modified phenolic resin (polyvalent phenolic compound in which a phenolic nucleus is linked by melamine, benzoguanamine, or the like), and an alkoxy group-containing aromatic ring-modified novolak resin (polyvalent phenolic compound in which a phenolic nucleus and an alkoxy group-containing aromatic ring are linked by a formaldehyde).

In the case of using other curing agents for epoxy resin, the blending proportion between the compound containing a phenolic hydroxyl group or the phenolic resin of the present invention and other curing agents for epoxy resin is not particularly limited as long as the characteristics of the compound containing a phenolic hydroxyl group of the application which exhibits excellent heat resistance and flame retardancy in terms of a cured product thereof are not impaired, and, for example, the compound containing a phenolic hydroxyl group or the phenolic resin of the present invention is preferably within a range of 5 parts by mass to 95 parts by mass in 100 parts by mass of the total mass of both.

In addition, in the case of using other curing agents for epoxy resin, the blending proportion with the epoxy resin is preferably a proportion in which the equivalent ratio (active hydrogen atom/epoxy group) between the total of active hydrogen atoms contained in the compound containing a phenolic hydroxyl group or the phenolic resin of the present invention and other curing agent for epoxy resin, and the epoxy group contained in the epoxy resin is 1/0.5 to 1/1.5 since reactivity and heat resistance of the cured product are excellent at this proportion.

In the curable composition of the present invention, a curing promoter can also be suitably used in combination as necessary. As the curing promoter, various curing promoters can be used, and examples thereof include phosphorus-based compounds, tertiary amines, imidazoles, organic acid metal salts, Lewis acids, and amine complex salts. In particular, in the case of using the curing promoter as semi-conductor sealing material applications, 2-ethyl-4-methyl-imidazole as the imidazole compounds, triphenylphosphine as the phosphorus-based compounds, and 1,8-diazabicyclo-[5.4.0]-undecene (DBU) as the tertiary amines are preferable from the viewpoint of excellent curing properties, heat resistance, electrical characteristics, and moisture resistance reliability.

The curable composition of the present invention described above may further contain other additive components depending on the applications or the desired performance. Specifically, for the purposes of further improving flame retardancy, a non-halogen-based flame retardant which substantially does not contain a halogen atom may be blended.

Examples of the non-halogen-based flame retardant include a phosphorus-based flame retardant, a nitrogen-based flame retardant, a silicone-based flame retardant, an inorganic flame retardant, and an organometallic salt-based flame retardant. These may be used alone respectively, or plural types thereof may be used in combination.

As the phosphorus-based flame retardant, any one of an inorganic flame retardant and an organic flame retardant can be used, and examples of the inorganic flame retardant include inorganic nitrogen-containing phosphorus compounds such as ammonium phosphates including red phosphorus, monoammonium phosphate, diammonium phosphate, triammonium phosphate, and ammonium polyphosphate, and phosphoric amides.

The red phosphorus is preferably subjected to a surface treatment for the purpose of preventing hydrolysis or the like, and examples of the surface treatment method include (i) a method for coat-treating with an inorganic compound such as magnesium hydroxide, aluminum hydroxide, zinc hydroxide, titanium hydroxide, bismuth oxide, bismuth hydroxide, bismuth nitrate, or a mixture thereof, (ii) a method for coat-treating with an inorganic compound such as magnesium hydroxide, aluminum hydroxide, zinc hydroxide, or titanium hydroxide, and a mixture of a thermosetting resin such as a phenolic resin, and (iii) a method for doubly coat-treating the surface of a coated film of an inorganic compound such as magnesium hydroxide, aluminum hydroxide, zinc hydroxide, or titanium hydroxide with a thermosetting resin such as a phenolic resin.

Examples of the organic phosphorus-based compound include general-purpose organic phosphorus-based compounds such as a phosphoric acid ester compound, a phosphonic acid compound, a phosphinic acid compound, a phosphine oxide compound, a phosphorane compound, and an organic nitrogen-containing phosphorus compound, and cyclic organic phosphorus compounds such as 9,10-dihydro-9-oxa-10-phosphaphenanthrene-10-oxide, 10-(2,5-dihydroxyphenyl)-10H-9-oxa-10-phosphaphenanthrene-10-oxide, and 10-(2,7-dihydroxynaphthyl)-10H-9-oxa-10-phosphaphenanthrene-10-oxide, and derivatives obtained by reacting this with a compound such as an epoxy resin or a phenolic resin.

The blending amount thereof is suitably selected depending on the type of a phosphorus-based flame retardant, other components of a curable composition, and the desired degree of flame retardancy, and for example, in the case of using red phosphorus as a non-halogen-based flame retardant, the red phosphorus is preferably blended within a range of 0.1 parts by mass to 2.0 parts by mass, and in the case of using an organic phosphorus compound, the organic phosphorus compound is preferably blended within a range of 0.1 parts by mass to 10.0 parts by mass, and particularly preferably blended within a range of 0.5 parts by mass to 6.0 parts by mass, in 100 parts by mass of the curable composition obtained by blending all of a compound containing a phenolic hydroxyl group or a phenolic resin, a curing agent, and other additives, or a filler.

The blending amount thereof is suitably selected depending on the type of a phosphorus-based flame retardant, other components of a curable composition, and the desired degree of flame retardancy, and for example, in the case of using red phosphorus as a non-halogen-based flame retardant, the red phosphorus is preferably blended within a range of 0.1 parts by mass to 2.0 parts by mass, and in the case of using an organic phosphorus compound, the organic phosphorus compound is preferably blended within a range of 0.1 parts by mass to 10.0 parts by mass, and particularly preferably blended within a range of 0.5 parts by mass to 6.0 parts by mass, in 100 parts by mass of the curable composition.

In addition, in the case of using the phosphorus-based flame retardant, the phosphorus-based flame retardant may be used in combination with hydrotalcite, magnesium hydroxide, a boron compound, zirconium oxide, black dye, calcium carbonate, zeolite, zinc molybdate, or activated charcoal.

Examples of the nitrogen-based flame retardant include a triazine compound, a cyanuric acid compound, an isocyanuric acid compound, and phenothiazine, and the triazine compound, the cyanuric acid compound, or the isocyanuric acid compound is preferable.

Examples of the triazine compound include (i) aminotriazine sulfate compounds such as guanylic melamine sulfate, melem sulfate, and melam sulfate, (ii) co-condensates of a phenol-base compound such as phenol, cresol, xylenol, butylphenol, or nonylphenol, and melamines such as melamine, benzoguanamine, acetoguanamine, or formguanamine and formaldehyde, (iii) a mixture of the co-condensates of (ii) and phenolic resins such as a phenolformaldehyde condensate or the like, (iv) a product obtained by further modifying (ii) and (iii) with tung oil or isomerized linseed oil, or the like, in addition to melamine, acetoguanamine, benzoguanamine, melon, melam, succinoguanamine, ethylene dimelamine, melamine polyphosphate, and triguanamine.

Examples of the cyanuric acid compound can include cyanuric acid and melamine cyanurate.

The blending amount of the nitrogen-based flame retardant is suitably selected depending on the type of the nitrogen-based flame retardant, other components of a curable composition, and the desired degree of flame retardancy, and for example, the nitrogen-based flame retardant is preferably blended within a range of 0.05 parts by mass to 10 parts by mass, and particularly preferably blended within a range of 0.1 parts by mass to 5 parts by mass, in 100 parts by mass of the curable composition.

In addition, when using the nitrogen-based flame retardant, metal hydroxide or a molybdenum compound may be used in combination.

The silicone-based flame retardant can be used without any particular limitation as long as the silicone-based flame retardant is an organic compound containing a silicon atom, and examples thereof include silicone oil, silicone rubber, and silicone resins.

The blending amount of the silicone-based flame retardant is suitably selected depending on the type of the silicone-based flame retardant, other components of a curable composition, and the desired degree of flame retardancy, and for example, the silicone-based flame retardant is preferably blended within a range of 0.05 parts by mass to 20 parts by mass in 100 parts by mass of the curable composition. In addition, when using the silicone-based flame retardant, a molybdenum compound or alumina may be used in combination.

Examples of the inorganic flame retardant include metal hydroxides, metal oxides, metal carbonate compounds, metal powder, boron compounds, and low melting point glass.

Examples of the metal hydroxide can include aluminum hydroxide, magnesium hydroxide, dolomite, hydrotalcite, calcium hydroxide, barium hydroxide, and zirconium hydroxide.

Examples of the metal oxide can include zinc molybdate, molybdenum trioxide, zinc stannate, tin oxide, aluminum oxide, iron oxide, titanium oxide, manganese oxide, zirconium oxide, zinc oxide, molybdenum oxide, cobalt oxide, bismuth oxide, chromium oxide, nickel oxide, copper oxide, and tungsten oxide.

Examples of the metal carbonate compound can include zinc carbonate, magnesium carbonate, calcium carbonate, barium carbonate, basic magnesium carbonate, aluminum carbonate, iron carbonate, cobalt carbonate, and titanium carbonate.

Examples of the metal powder can include aluminum powder, iron powder, titanium powder, manganese powder, zinc powder, molybdenum powder, cobalt powder, bismuth powder, chromium powder, nickel powder, copper powder, tungsten powder, and tin powder.

Examples of the boron compound can include zinc borate, zinc metaborate, barium metaborate, boric acid, and borax.

Examples of the low melting point glass can include glass-like compounds such as a Ceepree (Bokusui Brown Co., Ltd.) glass, a hydrated glass $SiO_2$—MgO—$H_2O$, PbO—$B_2O_3$-based glass, a ZnO—$P_2O_5$—MgO-based glass, a $P_2O_5$—$B_2O_3$—PbO—MgO-based glass, a P—Sn—O—F-based glass, a PbO—$V_2O_5$—$TeO_2$-based glass, an $Al_2O_3$—$H_2O$-based glass, and lead borosilicate-based glass.

The blending amount of the inorganic flame retardant is suitably selected depending on the type of the inorganic flame retardant, other components of a curable composition, and the desired degree of flame retardancy, and for example, the inorganic flame retardant is preferably blended within a range of 0.5 parts by mass to 50 parts by mass, and particularly preferably blended within a range of 5 parts by mass to 30 parts by mass in 100 parts by mass of the curable composition.

Examples of the organometallic salt-based flame retardant include ferrocene, an acetylacetonate metal complex, an organometallic carbonyl compound, an organic cobalt salt compound, an organic sulfonic acid metal salt, and a compound obtained by an ionic bond or a coordination bond of a metal atom to an aromatic compound or a heterocyclic compound.

The blending amount of the organometallic salt-based flame retardant is suitably selected depending on the type of the organometallic salt-based flame retardant, other components of a curable composition, and the desired degree of flame retardancy, and for example, the organometallic salt-based flame retardant is preferably blended within a range of 0.005 parts by mass to 10 parts by mass in 100 parts by mass of the curable composition.

In addition, various compounding agents such as a silane coupling agent, a release agent, a pigment, and an emulsifier can be added to the curable composition of the present invention, as necessary.

In the curable composition of the present invention, an inorganic filler can be blended, as necessary. Since the compound containing a phenolic hydroxyl group and the phenolic resin used in the present invention has low melt viscosity, it is possible to increase the blending amount of an inorganic filler, and such a curable composition can be suitably used in particularly semiconductor sealing material applications.

Examples of the inorganic filler include fused silica, crystalline silica, alumina, silicon nitride, and aluminum hydroxide. Among these, the fused silica is preferable since greater amount of the inorganic filler can be blended. The fused silica can be used in any one of a crushed shape or a spherical shape; however, in order to increase the blending amount of the fused silica and to suppress increase in melt viscosity of the curable composition, spherical silica is preferably mainly used. Furthermore, in order to increase the blending amount of the spherical silica, the particle size distribution of the spherical silica is preferably suitably adjusted. The filling ratio is preferably within a range of 0.5 parts by mass to 95 parts by mass in 100 parts by mass of the curable composition.

In addition, in the case of using the curable composition of the present invention in applications such as a conductive paste, it is possible to use a conductive filler such as silver powder or copper powder.

In the case of preparing the curable composition of the present invention in a varnish for a printed circuit board, an organic solvent is preferably blended. Examples of the organic solvent capable of being used here include methyl ethyl ketone, acetone, dimethylformamide, methyl isobutyl ketone, methoxypropanol, cyclohexanone, methyl cellosolve, ethyl diglycol acetate, and propylene glycol monomethyl ether acetate, and the selection and the suitable amount to be used can be suitably selected depending on the application, and, for example, in printed circuit board applications, polar solvents such as methyl ethyl ketone, acetone, and dimethylformamide having the boiling point of 160° C. or lower are preferable, and the solvents are preferably used in a proportion in which the non-volatile content becomes 40% by mass to 80% by mass. On the other hand, in adhesive film applications for build-up, as the organic solvent, for example, ketones such as acetone, methyl ethyl ketone, and cyclohexanone, acetic acid esters such as ethyl acetate, butyl acetate, cellosolve acetate, propylene glycol monomethyl ether acetate, and carbitol acetate, carbitols such as cellosolve and butyl carbitol, aromatic hydrocarbons such as toluene and xylene, dimethylformamide, dimethylacetamide, or N-methylpyrrolidone are preferably used, and the solvents are preferably used in a proportion in which the non-volatile content becomes 30% by mass to 60% by mass.

The curable composition of the present invention is obtained by uniformly mixing the respective components described above. The curable composition of the present invention obtained by blending a compound containing a phenolic hydroxyl group or a resin, a curing agent, and as necessary, a curing promoter can be easily cured by the same methods known in the related art, whereby a cured product is formed. Examples of the cured product include molded cured products such as a laminate, a cast material, an adhesive layer, a coating film, and a film.

Since the compound containing a phenolic hydroxyl group and the phenolic resin of the present invention exhibit excellent heat resistance and flame retardancy in terms of a cured product thereof, the compound containing a phenolic hydroxyl group and the phenolic resin can be used in various electronic material applications. Among these, in particular, the compound containing a phenolic hydroxyl group and the phenolic resin can be suitably used in semiconductor sealing material applications.

The semiconductor sealing material can be prepared by a method in which a mixture of a phenol component including the compound containing a phenolic hydroxyl group or the phenolic resin of the present invention, a curing agent, and a filler is sufficiently mixed until it becomes uniform using an extruder, a kneader, or a roll. As the filler used here, the inorganic fillers described above are exemplified, and, as described above, the filler is preferably used within a range of 0.5 parts by mass to 95 parts by mass in 100 parts by mass of the curable composition. Among these, the filler is preferably used within a range of 70 parts by mass to 95 parts by mass, and particularly preferably used within a range of 80 parts by mass to 95 parts by mass, since flame retardancy, moisture resistance, and soldering crack resistance are improved, and a linear expansion coefficient can be reduced.

As a method for molding a semiconductor package using the obtained semiconductor sealing material, a method in which the semiconductor sealing material is formed using a casting, a transfer forming machine, or an injection molding machine, and the resultant product is heated for 2 hours to 10 hours under temperature conditions of 50° C. to 200° C. is exemplified, and by such a method, it is possible to obtain a semiconductor device which is a molded product.

In addition, in production of a printed circuit board using the compound containing a phenolic hydroxyl group or the phenolic resin of the present invention, a method which includes impregnating a reinforcement basic material with a varnish-like curable composition including the compound containing a phenolic hydroxyl group or the phenolic resin of the present invention, a curing agent, an organic solvent, and other additives, and superposing a copper foil on the resulting material, followed by heat-pressing is exemplified. Examples of the reinforcement basic material capable of being used here include paper, glass cloth, glass nonwoven fabric, aramid paper, aramid cloth, glass mat, and glass roving cloth. In describing the method in more detail, first, the varnish-like curable composition described above is heated at a heating temperature according to the solvent species used, preferably 50° C. to 170° C., whereby prepreg is obtained which is a cured product. The mass proportion between the curable composition and the reinforcement basic material used at this time is not particularly limited; however, typically, the prepreg is preferably prepared such that the resin content in the prepreg is 20% by mass to 60% by mass. Next, the prepreg obtained in the above manner is laminated by an ordinary method, then, copper foil is suitably superposed thereon, and the resultant product is heat-pressed at 170° C. to 250° C. for 10 minutes to 3 hours under a pressure of 1 MPa to 10 MPa, whereby a desired printed circuit board is obtained.

EXAMPLES

Hereinafter, the present invention will be more specifically described using examples and comparative examples, and "parts" and "%" below are based on mass unless otherwise specifically indicated. Moreover, a softening point, GPC, NMR, an MS spectrum were measured under the following conditions.

Softening point measurement method: based on JIS K7234.

GPC: the measurement conditions are as follows.
Measurement apparatus: "HLC-8220 GPC" manufactured by Tosoh Corporation
Column: guard column "HXL-L" manufactured by Tosoh Corporation
+"TSK-GEL G2000HXL" manufactured by Tosoh Corporation
+"TSK-GEL G2000HXL" manufactured by Tosoh Corporation
+"TSK-GEL G3000HXL" manufactured by Tosoh Corporation
+"TSK-GEL G4000HXL" manufactured by Tosoh Corporation
Detector: RI (differential refractometer)
Data processing: "GPC-8020 model II Version 4.10" manufactured by Tosoh Corporation Measurement conditions: column temperature 40° C.
　　eluent: tetrahydrofuran
　　flow rate 1.0 ml/min
Standard: according to the measurement manual the "GPC-8020 model II Version 4.10", the following monodisperse polystyrene of which the molecular weight is known is used.
　　(Polystyrene Used)
　　"A-500" manufactured by Tosoh Corporation
　　"A-1000" manufactured by Tosoh Corporation
　　"A-2500" manufactured by Tosoh Corporation
　　"A-5000" manufactured by Tosoh Corporation
　　"F-1" manufactured by Tosoh Corporation
　　"F-2" manufactured by Tosoh Corporation
　　"F-4" manufactured by Tosoh Corporation
　　"F-10" manufactured by Tosoh Corporation
　　"F-20" manufactured by Tosoh Corporation
　　"F-40" manufactured by Tosoh Corporation
　　"F-80" manufactured by Tosoh Corporation
　　"F-128" manufactured by Tosoh Corporation
Sample: a solution (50 μl) obtained by filtering a tetrahydrofuran solution of 1.0% by mass in terms of the resin solid content through a microfilter.
$^{13}$C-NMR: the measurement conditions are as follows.
Apparatus: AL-400 manufactured by JEOL Ltd.
Measurement mode: SGNNE (1H complete decoupling method of NOE elimination)
Solvent: dimethylsulfoxide
Pulse angle: 45° pulse
Sample concentration: 30% by weight
Cumulated number: 10,000 times
　　MS: double focusing mass spectrometer "AX505H (FD505H)" manufactured by JEOL Ltd.

Example 1

Preparation of Phenolic Resin (1)

240 parts by mass (1.5 mol) of 2,7-dihydroxynaphthalene, 162 parts by mass (1.5 mol) of parabenzoquinone, 268 parts by mass of isopropyl alcohol, and 8 parts by mass of oxalic acid were put into a flask equipped with a thermometer, a dropping funnel, a cooling tube, a fractionating column, and a stirrer, and the resultant product was heated from room temperature to 120° C. with stirring. After the temperature reached 120° C., stirring was performed for 2 hours to react. After the reaction ended, the resultant product was dried over under reduced pressure by being heated to 180° C., whereby 359 parts by mass of a phenol intermediate (5) was obtained. A GPC chart of the obtained phenol intermediate is shown in FIG. 1, a $^{13}$CNMR spectrum of the obtained phenol intermediate is shown in FIG. 2, and an MS spectrum of the obtained phenol intermediate is shown in FIG. 3. The hydroxyl equivalent of the phenol intermediate (5) was 68 g/eq, and the softening point of the phenol intermediate (5) was 126° C. A peak of 268 corresponding to the binuclear compound (x1) represented by the following Structural Formula (a-1) and a peak of 426 corresponding to the trinuclear compound (x2) represented by the following Structural Formula (b-1) were detected from the MS spectrum. The content of the component corresponding to the binuclear compound (x1) in the phenolic resin, calculated from the GPC chart was 43.6%, and the content of the component corresponding to the trinuclear compound (x2) was 30.7%.

[Chem. 23]

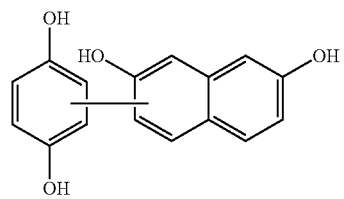
(a-1)

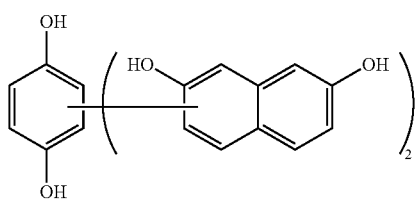
(b-1)

Example 2

Preparation of Phenolic Resin (2)

160 parts by mass (1.0 mol) of 2,7-dihydroxynaphthalene, 158 parts by mass (1.0 mol) of naphthoquinone, and 318 parts by mass of methyl isobutyl ketone were put into a flask equipped with a thermometer, a dropping funnel, a cooling tube, a fractionating column, and a stirrer, and the resultant product was heated from room temperature to 150° C. with stirring. After the temperature reached 150° C., stirring was performed for 3 hours to react. After the reaction ended, the resultant product was dried over under reduced pressure by being heated to 180° C., whereby 300 parts by mass of a phenol intermediate (6) was obtained. A GPC chart of the obtained phenol intermediate is shown in FIG. 4, and an MS spectrum of the obtained phenol intermediate is shown in FIG. 5. The hydroxyl equivalent of the phenol intermediate (6) was 101 g/eq, and the softening point of the phenol intermediate (6) was 130° C. A peak of 318 corresponding to the binuclear compound (x1) represented by the following Structural Formula (a-2) and a peak of 300 corresponding to the dinaphthofuran compound represented by the following Structural Formula (c) were detected from the MS spectrum. The content of the component corresponding to the binuclear compound (x1) in the phenolic resin, calculated from the GPC chart was 49.7%, and the content of the dinaphthofuran compound represented by the following Structural Formula (c) was 6.0%.

[Chem. 24]

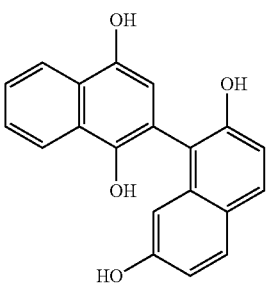
(a-2)

-continued

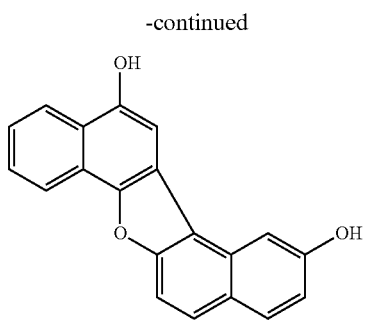
(c)

Examples 3 and 4 and Comparative Example 1

Evaluation test of heat resistance and flame retardancy was performed on the phenolic resins (1) and (2) obtained above, and a phenolic resin (1') for comparison [triphenyl-methane type phenolic resin ("MEH-7500" manufactured by Meiwa Plastic Industries, Ltd., hydroxyl equivalent of 98 g/eq)] in the following manner.

<Evaluation of Heat Resistance>

1) Production of Evaluation Sample

Any one of the phenolic resins (1), (2), and (1'), a naphthalene type epoxy resin ("EXA-4750" manufactured by DIC Corporation, epoxy equivalent of 188 g/eq) as a curing agent, and triphenylphosphine (hereinafter, abbreviated as "TPP") as a curing promoter were blended according to the composition ratios shown in the following Table 2, whereby curable compositions were obtained. Each of these was poured into a mold of 11 cm×9 cm×2.4 mm and molded at a temperature of 150° C. for 10 minutes using a press. After the molded product was taken out from the mold, the molded product was cured at a temperature of 175° C. for 5 hours, whereby an evaluation sample was obtained.

2) Measurement of Glass Transition Temperature

A measurement of the temperature at which the change in elastic modulus becomes maximum (at which tan δ change ratio is the greatest) was performed on the evaluation sample using a viscoelasticity measuring apparatus (DMA: solid viscoelasticity measuring apparatus RSAII manufactured by Rheometric Scientific Inc., rectangular tension method; frequency of 1 Hz, temperature raising rate of 3° C./min), and this is evaluated as the glass transition temperature. The results are shown in Table 1.

TABLE 1

|  | Example 3 | Example 4 | Comparative Example 1 |
|---|---|---|---|
| Phenolic resin (1) | 26.6 |  |  |
| Phenolic resin (2) |  | 34.9 |  |
| MEH-7500 |  |  | 34.3 |
| EXA-4750 | 73.4 | 65.1 | 65.7 |
| TPP | 1.0 | 1.0 | 1.0 |
| Heat resistance (° C.) | 245 | 232 | 215 |

<Evaluation of Flame Retardancy>

1) Production of Evaluation Sample

Any one of the phenolic resins (1), (2), and (1'), a naphthalene type epoxy resin ("EXA-4750" manufactured by DIC Corporation, epoxy equivalent of 188 g/eq) as a curing agent, triphenylphosphine (hereinafter, abbreviated as "TPP") as a curing promoter, spherical silica ("FB-5604" manufactured by Denki Kagaku Kogyo Kabushiki Kaisha) as an inorganic filler, a coupling agent ("KBM-403" manufactured by Shin-Etsu Chemical Co., Ltd.) as a silane coupling agent, carnauba wax ("PEARL WAX No. 1-P" manufactured by Cerarica Noda Co., Ltd.), and carbon black were blended according to the composition ratios shown in the following Table 3, and the resultant products were melted and kneaded at a temperature of 85° C. for 5 minutes using a two roll, whereby curable compositions were obtained. Using the obtained curable composition, a sample having a size of 12.7 mm in width, 127 mm in length and 1.6 mm in thickness was molded at a temperature of 175° C. for 90 seconds using a transfer molding machine, and the sample was cured at a temperature of 175° C. for 5 hours, whereby an evaluation sample was obtained.

2) Evaluation of Flame Retardancy

A combustion test was performed on the five samples for evaluation having a thickness of 1.6 mm obtained in the above according to the UL-94 test method. The results are shown in Table 2.

Flame Retardant Test Class

*1: maximum combustion time (seconds) in a single flame contact

*2: total combustion time (seconds) of five test pieces

TABLE 2

|  | Example 3 | Example 4 | Comparative Example 1 |
|---|---|---|---|
| Phenolic resin (1) | 31.3 |  |  |
| Phenolic resin (2) |  | 41.2 |  |
| MEH-7500 |  |  | 40.4 |
| EXA-4750 | 86.7 | 76.8 | 77.6 |
| TPP | 2 | 2 | 2 |
| Spherical silica | 870 | 870 | 870 |
| Coupling agent | 4 | 4 | 4 |
| Carnauba wax | 4 | 4 | 4 |
| Carbon black | 2 | 2 | 2 |
| Flame retardant test class | V-0 | V-0 | Combustion |
| *1 | 9 | 7 | 38 |
| *2 | 45 | 42 | 266 |

The invention claimed is:

1. A compound containing a phenolic hydroxyl group, which has a molecular structure represented by the following General Formula (I):

[Chem. 1]

(I)

wherein X is a structural site represented by the following Structural Formula (x1) or (x2);

[Chem. 2]

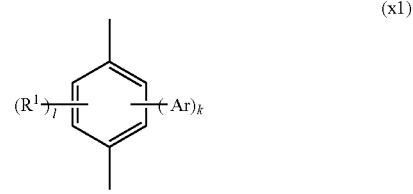
(x1)

-continued

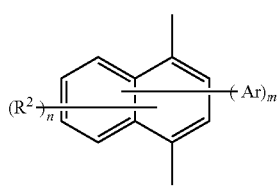
(x2)

wherein, in Formula (x1) or (x2), each of $R^1$ and $R^2$ is any one of an alkyl group having 1 to 4 carbon atoms, an alkoxy group having 1 to 4 carbon atoms, an aryl group, and an aralkyl group, l is an integer of 0 to 3, n is an integer of 0 to 4, in a case where l or n is 2 or greater, a plurality of $R^1$'s or $R^2$'s may be the same as or different from each other, k is an integer of 1 to 3, m is 1 or 2, Ar is a structural site represented by the following Structural Formulas (Ar1):

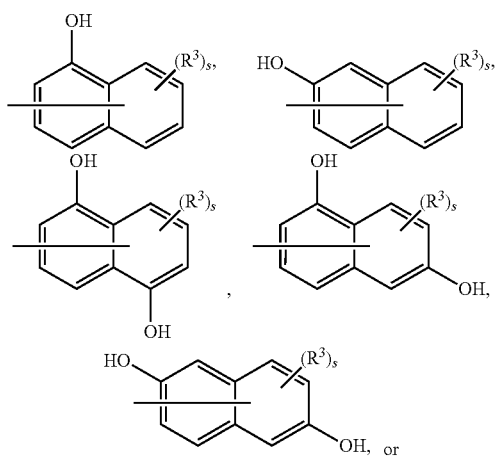

-continued

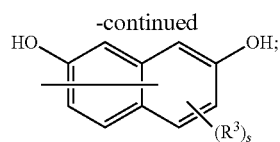

wherein in a case where k or m is 2 or greater, a plurality of Ar's may be the same as or different from each other; and wherein, $R^3$ is any one of an alkyl group having 1 to 4 carbon atoms, an alkoxy group having 1 to 4 carbon atoms, an aryl group, and an aralkyl group, $R^3$ may be bonded to either of two aromatic nuclei, s is an integer of 0 to 6, in a case where s is 2 or greater, a plurality of $R^3$'s may be the same as or different from each other, and r is 1 or 2.

2. A phenolic resin, comprising:
   the compound containing a phenolic hydroxyl group according to claim 1.

3. A curable composition, comprising as essential components:
   the compound containing a phenolic hydroxyl group according to claim 1; and
   a curing agent.

4. A cured product which is obtained by a curing reaction of the curable composition according to claim 3.

5. A semiconductor sealing material, comprising:
   the curable composition according to claim 3; and
   an inorganic filler.

6. A printed circuit board obtained by impregnating a reinforcement basic material with a resin composition varnished by blending the curable composition according to claim 3 with an organic solvent, and superposing a copper foil on the resulting material, followed by heat-pressing.

* * * * *